(12) United States Patent
Hornbaek et al.

(10) Patent No.: US 9,485,992 B2
(45) Date of Patent: Nov. 8, 2016

(54) **BIOPROTECTION USING *LACTOBACILLUS RHAMNOSUS* STRAINS**

(71) Applicant: Chr. Hansen A/S, Hoersholm (DK)

(72) Inventors: Tina Hornbaek, Birkeroed (DK); Maike Lisberg, Espergaerde (DK); Silja Kej Diemer, Frederiksberg (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 14/390,231

(22) PCT Filed: Apr. 9, 2013

(86) PCT No.: PCT/EP2013/057410
§ 371 (c)(1),
(2) Date: Oct. 2, 2014

(87) PCT Pub. No.: WO2013/153074
PCT Pub. Date: Oct. 17, 2013

(65) Prior Publication Data
US 2015/0079057 A1 Mar. 19, 2015

Related U.S. Application Data

(63) Continuation-in-part of application No. PCT/EP2012/056384, filed on Apr. 9, 2012.

(30) Foreign Application Priority Data

Apr. 9, 2012 (EP) .................................... 12163508
May 22, 2012 (EP) .................................... 12168977
Feb. 8, 2013 (EP) .................................... 13154591

(51) Int. Cl.
| | | |
|---|---|---|
| A01N 63/00 | (2006.01) |
| A23L 1/30 | (2006.01) |
| A23C 9/123 | (2006.01) |
| A23L 3/3571 | (2006.01) |
| A61K 35/747 | (2015.01) |
| C12N 1/20 | (2006.01) |
| C12R 1/225 | (2006.01) |
| A23B 4/22 | (2006.01) |
| A23C 19/032 | (2006.01) |
| A23C 19/076 | (2006.01) |
| A23C 9/158 | (2006.01) |

(52) U.S. Cl.
CPC ............... *A01N 63/00* (2013.01); *A23B 4/22* (2013.01); *A23C 9/1234* (2013.01); *A23C 9/1585* (2013.01); *A23C 19/0323* (2013.01); *A23C 19/076* (2013.01); *A23L 1/3014* (2013.01); *A23L 3/3571* (2013.01); *A61K 35/747* (2013.01); *C12N 1/20* (2013.01); *C12R 1/225* (2013.01); *A23V 2002/00* (2013.01); *A23Y 2220/63* (2013.01); *A23Y 2220/73* (2013.01)

(58) Field of Classification Search
CPC ..................................................... A23L 1/3014
See application file for complete search history.

(56) References Cited

U.S. PATENT DOCUMENTS

| | | |
|---|---|---|
| 5,378,458 A | 1/1995 | Mayra-Makinen et al. |
| 5,965,414 A | 10/1999 | Vandenbergh et al. |
| 2005/0095318 A1 | 5/2005 | Schwenninger et al. |
| 2005/0271640 A1 | 12/2005 | Suomalainen et al. |
| 2008/0107699 A1 | 5/2008 | Spigelman et al. |
| 2011/0045134 A1 | 2/2011 | Perrier et al. |
| 2014/0093487 A1 | 4/2014 | Hornbaek et al. |

FOREIGN PATENT DOCUMENTS

| | | |
|---|---|---|
| CN | 101613667 A | 12/2009 |
| EP | 0 221 499 A2 | 5/1987 |
| EP | 0 302 300 A2 | 2/1989 |
| EP | 0 516 780 A2 | 1/1994 |
| EP | 0 852 114 A1 | 7/1998 |
| EP | 1 308 506 A1 | 5/2003 |
| EP | 1 442 113 | 5/2003 |
| EP | 1 992 351 A1 | 11/2008 |
| JP | 2011-505162 A | 2/2011 |
| WO | WO-03/040349 A1 | 5/2003 |
| WO | WO-03/070203 A1 | 8/2003 |
| WO | WO-03/070260 A1 | 8/2003 |
| WO | WO-2004/041305 A1 | 5/2004 |
| WO | WO-2007/140621 A1 | 12/2007 |
| WO | WO-2009/098411 A2 | 8/2009 |
| WO | WO-2012/136830 A1 | 10/2012 |

(Continued)

OTHER PUBLICATIONS

Office Action dated Jun. 16, 2015 issued in U.S. Appl. No. 14/110,388.
U.S. Appl. No. 14/390,238, filed Oct. 2, 2014, Hornbaek et al.

(Continued)

*Primary Examiner* — Bin Shen
(74) *Attorney, Agent, or Firm* — Foley & Lardner LLP

(57) ABSTRACT

The present invention is related to the field of bioprotection, in particular to the strain of *Lactobacillus rhamnosus* CHCC5366 with accession no. DSM23035. Furthermore, the present invention concerns an antifungal composition comprising the strain, an antifungal composition comprising the strain and at least one strain of *Lactobacillus paracasei*, food, feed and pharmaceutical products comprising such an antifungal composition, a method of manufacturing such food, feed and pharmaceutical products, a method for reducing the content of yeasts and molds of such food, feed and pharmaceutical products and uses of the antifungal composition.

16 Claims, 7 Drawing Sheets

(56) References Cited

FOREIGN PATENT DOCUMENTS

| WO | WO-2013/153070 A1 | 10/2013 |
| WO | WO-2013/153074 A1 | 10/2013 |

OTHER PUBLICATIONS

Danisco A/S, "HOLDBAC-TM YM Protective Cultures", 2008, Retrieved from www.foodnavigator.com/content/.../Daniscocultures-FN-wk14-2008.pdf, 4 pages.
European Search Report dated Jun. 28, 2012, issued in European Application No. 12168977.2.
European Search Report dated Sep. 10, 2012 issued in European Application No. 12163509.8.
European Search Report dated Nov. 22, 2012 issued in European Application No. 12168971.5.
European Search Report dated Jul. 14, 2011 issued in European Application No. 11161609.0.
European Search Report dated Sep. 10, 2012 issued in European Application No. 12163508.0.
Hassan et al., "Antifungal activity of *Lactobacillus paracasei* ssp. tolerans isolated from a sourdough bread culture", International Journal of Food Microbiology, vol. 121, No. 1, pp. 112-115, 2008.
International Search Report dated May 22, 2013 issued in PCT/EP2013/057400.
International Search Report dated May 22, 2013 issued in PCT/EP2013/057410.
International Search Report dated May 7, 2012 issued in PCT/EP2012/056384.
Kosikowski, F.V. et al., "Cheese and Fermented Milk Foods", 1997, 3rd Ed. F.V. Kosikowski, L.L.C. Westport, CT, pp. 109-126, vol. 1, chapter 7.
Written Opinion mailed May 22, 2013 issued in PCT/EP2013/057400.
Schnürer J et al., "Antifungal lactic acid bacteria as biopreservatives", Trends in Food Science and Technology, vol. 16, No. 1-3, 2005, pp. 70-78.
Schwenninger et al., "A Mixed Culture of *Propionibacterium jensenii* and *Lactobacillus paracasei* subsp. *paracasei* Inhibits Food Spoilage Yeasts", Systematic and Applied Microbiology, vol. 27, 2004, pp. 229-237.
Schwenninger et al., "Detection of antifungal properties in *Lactobacillus paracasei* subsp. *paracasei* SM20, SM29, and SM63 and molecular typing of the strains", Journal of Food Protection, vol. 68, No. 1, 2005, pp. 111-119.
Tharmaraj et al., "Antimicrobial effects of probiotic bacteria against selected species of yeasts and moulds in chese-based dips." International Journal of Food Science, 2009, No. 44, pp. 1916-1926.
Voulgari K et al., "Antifungal activity of non-starter lactic acid bacteria isolates from dairy products", Food Control, vol. 21, No. 2, 2010, pp. 136-142.
Ju et al., "Review on the Function of Lactobacillus paracasei and application in food industry", China Dairy Industry, 37(8):48-50 (Dec. 2009), with English abstract attached.
Office action dated Mar. 3, 2015, issued in U.S. Appl. No. 14/110,388.
Office action dated Sep. 16, 2014 issued in Chinese Application No. 201280028255.8, with English translation.
International Preliminary Report on Patentability issued in application PCT/EP2012/056384 dated Oct. 8, 2013; 4 pages.
The State Intellectual Property Office of the People's Republic of China, First Office Action, Application 201380018783.X, dated Aug. 31, 2015 (with English translation); 21 pages.
USPTO Final Office Action issued in U.S. Appl. No. 14/110,388 (US 2014-0093487) dated Feb. 2, 2016; 14 pages.
Yang, Hong Mei, et al.; Study of Lactobacillus rhamnosus application in yoghurt; Xinjiang Animal Husbandry, 10:30-32; (Dec. 2011).
USPTO Restriction Requirement issued in U.S. Appl. No. 14/390,238 (US 2015-0064152) dated Aug. 1, 2016.

US 9,485,992 B2

BIOPROTECTION USING *LACTOBACILLUS RHAMNOSUS* STRAINS

CROSS REFERENCE TO RELATED APPLICATIONS

The present application is the U.S. National Stage of International Application No. PCT/EP2013/057410, filed on Apr. 9, 2013, and claims the benefit of priority under 35 USC §§119 and/or 120 to International Application No. PCT/EP2012/056384 filed on Apr. 9, 2012, European Patent Application No. 12163508.0 filed on Apr. 9, 2012, European Patent Application No. 12168977.2 filed on May 22, 2012, and European Patent Application No. 13154591.5 filed on Feb. 8, 2013.

FIELD OF THE INVENTION

The present invention is related to the field of bioprotection, in particular to the strain of *Lactobacillus rhamnosus* CHCC5366 with accession no. DSM23035. Furthermore, the present invention concerns an antifungal composition comprising the strain, an antifungal composition comprising the strain and at least one strain of *Lactobacillus paracasei*, food, feed and pharmaceutical products comprising such an antifungal composition, a method of manufacturing such food, feed and pharmaceutical products, a method for reducing the content of yeasts and molds of such food, feed and pharmaceutical products and uses of the antifungal composition.

BACKGROUND OF THE INVENTION

For many years lactic acid bacteria have been used for increasing the shelf life of food products. During fermentation the lactic acid bacteria produce lactic acids and other organic acids thereby reducing the pH of the food product making it unfavorable to the growth of unwanted microorganisms, such as pathogenic bacteria, yeasts and fungi.

Additionally, some lactic acid bacteria also produce metabolites with antimicrobial activity.

European Patent Application no. EP0221499 describes the antifungal properties of *Lactobacillus rhamnosus* NRRL-B-15972 which is capable of inhibiting the growth of different molds when cultured on agar medium supplemented with cucumber juice.

European Patent Application no. EP0576780 is related to *Lactobacillus rhamnosus* LC-705 which can inhibit the growth of *Penicillium, Cladosporium, Fusarium* and *Candida* on a lactoserum-based medium, supplemented with casein hydrolysate and with yeast extract.

European Patent Application no. EP1442113 is directed to mixtures of *Propionibacterium jensenii* and *Lactobacillus* sp., such as *Lactobacillus rhamnosus*, with antimicrobial activities for use for bioprotection.

However, there is still a need for bioprotective agents with an improved antifungal effect as single strains or in combination with other bioprotective strains.

SUMMARY OF THE INVENTION

The object of the present invention is the provision of novel strains of lactic acid bacteria with a high efficacy as bioprotective agents.

The present inventors have by extensive screening and research found that certain *Lactobacillus rhamnous* strains have a significantly higher effect against yeasts and molds as compared to commercial bioprotective cultures on the market as well as potassium sorbate, a commonly used chemical preservative.

The present inventors have further found that a certain group of lactic acid bacteria when combined with another group of lactic acid bacteria exhibit a significant synergistic antimicrobial effect. The antimicrobial effect of the two groups of bacteria combined, surprisingly, is greater than the sum of the individual effects of the two groups of bacteria.

DETAILED DESCRIPTION OF THE INVENTION

Definitions

Figure 1:
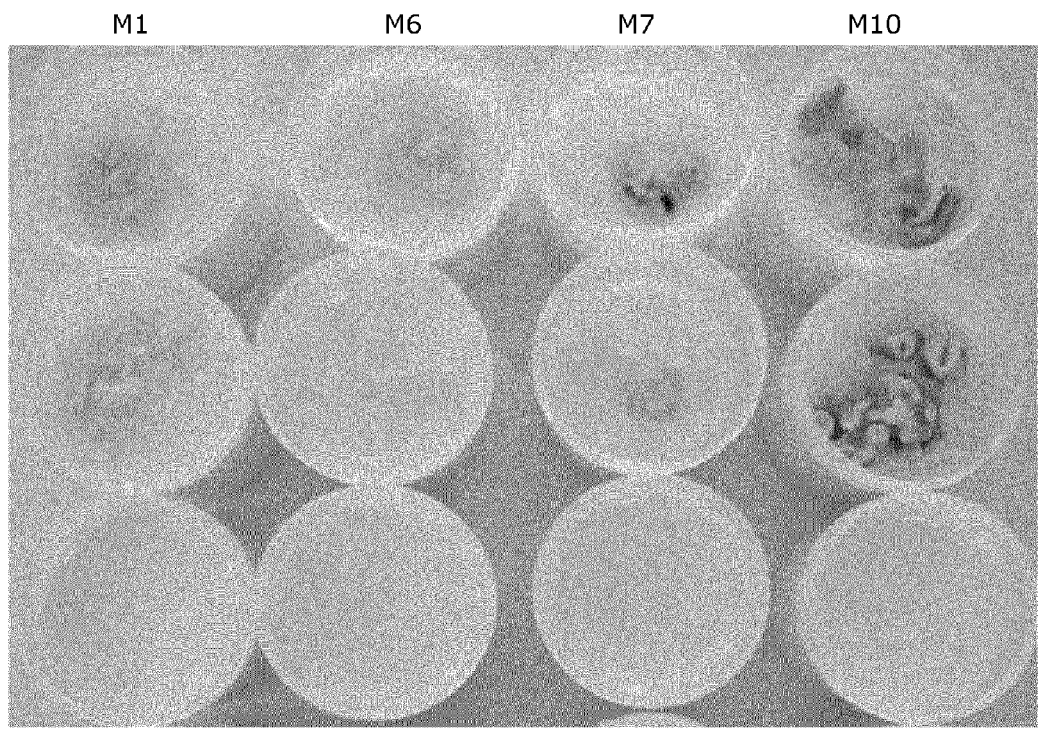
FIG. 1 depicts growth of molds in yoghurt with 1.5% fat fermented with a starter culture YF-L901 alone (top row), together with HOLDBAC™ YM-B (middle row) and together with *Lactobacillus rhamnosus* CHCC5366. The target contaminants were added in the concentrations mentioned in the text from left to right: *Penicillium brevicompactum* (M1), *Penicillium commune* (M6), Acromyrmex *Aspergillus versicolor* (M7) and *Penicillium crustosum* (M10), respectively. The yoghurts had been incubated at 7±1° C. for 45 days.

As used herein, the term "lactic acid bacterium" designates a gram-positive, microaerophilic or anaerobic bacterium, which ferments sugars with the production of acids including lactic acid as the predominantly produced acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp. and *Enterococcus* spp. These are frequently used as food cultures alone or in combination with other lactic acid bacteria.

The term "food" is meant to include also cheese. The term "cheese" is understood to encompass any cheese, including hard, semi-hard and soft cheeses, such as cheeses of the following types: Cottage, Feta, Cheddar, Parmesan, Mozzarella, Emmentaler, Danbo, Gouda, Edam, Feta-type, blue cheeses, brine cheeses, Camembert and Brie. The person skilled in the art knows how to convert the coagulum into cheese, methods can be found in the literature, see e.g. Kosikowski, F. V., and V. V. Mistry, "Cheese and Fermented Milk Foods", 1997, 3rd Ed. F. V. Kosikowski, L. L. C. Westport, Conn. As used herein, a cheese which has a NaCl concentration below 1.7% (w/w) is referred to as a "low-salt cheese".

Lactic acid bacteria, including bacteria of the species *Lactobacillus* sp. and *Lactococcus* sp., are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product or a cheese. Such lactic acid bacterial cultures are in general referred to as "starter cultures" or "starters".

The term "mesophile" herein refers to microorganisms that thrive best at moderate temperatures (15° C.-40° C.). The industrially most useful mesophilic bacteria include *Lactococcus* spp. and *Leuconostoc* spp. The term "mesophilic fermentation" herein refers to fermentation at a temperature between about 22° C. and about 35° C. The term "mesophilic fermented milk product" refers to fermented milk products prepared by mesophilic fermentation of a mesophilic starter culture and include such fermented milk products as buttermilk, sour milk, cultured milk, smetana, sour cream and fresh cheese, such as quark, tvarog and cream cheese.

The term "thermophile" herein refers to microorganisms that thrive best at temperatures above 43° C. The industrially most useful thermophilic bacteria include *Streptococcus* spp. and *Lactobacillus* spp. The term "thermophilic fermentation" herein refers to fermentation at a temperature above about 35° C., such as between about 35° C. to about 45° C. The term "thermophilic fermented milk product" refers to fermented milk products prepared by thermophilic fermentation of a thermophilic starter culture and include such fermented milk products as set-yoghurt, stirred-yoghurt and drinking yoghurt.

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of dairy products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid (such as a cheese) or liquid form (such as a fermented milk product).

The compositions of the invention provide the advantage that unwanted microorganisms selected from fungi, bacteria and mixtures thereof, for example on food, feed and pharmaceutical products and in humans and animals, can be inhibited. The prevention and/or inhibition of the growth of fungi, such as yeasts and molds, is particularly envisaged. Therefore, in a preferred embodiment, the term "antimicrobial" is to be understood as "antifungal".

The term "unwanted microorganisms" herein refers to microorganisms such as bacteria and fungi, such as yeasts, which are pathogenic and/or able to deteriorate food, feed or pharmaceutical products. The compositions of the invention provide the advantage that unwanted microorganisms selected from fungi, bacteria and mixtures thereof, for example on food, feed and pharmaceutical products and in humans and animals, can be inhibited. The prevention and/or inhibition of the growth of fungi, such as yeasts and molds, is particularly envisaged.

The terms "to inhibit" and "to be inhibiting" in relation to yeasts and molds mean for example that the growth or the number or the concentration of yeasts and molds, for example in food products and/or on the surface of food products comprising the strains according to the present invention, is lower than in food products and/or on the surface of food products which do not comprise such strains.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties (e.g. regarding antifungal properties) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and Aspects of the Invention

The present inventors have screened among 200 candidates of *Lactobacillus plantarum, Lactobacillus paracasei* and *Lactobacillus rhamnosus* to find the most efficient strains against a wide range of microorganisms, such as yeasts and molds.

Screenings were carried out in a model assay mimicking mesophilic fermented milk products as much as possible in milk-based media to which a relevant starter culture was added with or without bioprotective candidates and which was fermented under conditions relevant to mesophilic fermented milk products. Target organisms were isolated from mesophilic fermented milk products. Lactic acid bacteria purified from the HOLDBAC™ cultures from Danisco A/S, Denmark (which contain a mixture of *Lactobacillus* and *Propionibacterium freudenreichii* ssp. *shermanii* strains), as well as the complete HOLDBAC™ YM-B and HOLDBAC™ YM-C cultures (which, as noted above, contain both lactic acid bacteria and propionic acid bacteria) were used as bench mark.

The model assay is described in European Patent Application no. EP11161609.0.

Seventeen candidates among *Lactobacillus paracasei* and *Lactobacillus rhamnosus* were found generally to inhibit the 12 indicator fungi as well or better than the bench mark lactic acid bacteria when tested at 25° C.

When tested on yoghurt one strain of *Lactobacillus rhamnosus, Lactobacillus rhamnosus* strain CHCC5366 that was deposited with the German Collection of Microorganisms and Cell Cultures (DSMZ) under accession no. DSM23035 showed to be significantly better at inhibiting yeasts and molds than a commercially available bioprotective culture.

The inhibiting effect of the strain against the yeasts and molds could be determined by storing the fermented milk products at a suitable temperature during a suitable storage time as described in the Examples below.

In general, the suitable temperature at which this method should be performed depends on the temperature at which the specific food, feed or pharmaceutical product is normally stored and/or manufactured. The temperature at which the products are usually stored are between 5° C. and 26° C., preferably the temperature is about 8° C.

The storage time at the temperature depends on the time during which the food, feed, or pharmaceutical product is normally stored (shelf life). The storage time usually is 5-65, preferably 7-60 days, more preferably 7-28 days, and even more preferably the storage time is about 21 days.

Accordingly, a first aspect of the present invention relates to a *Lactobacillus rhamnosus* strain selected from the group consisting of the *Lactobacillus rhamnosus* strain CHCC5366 that was deposited with the German Collection of Microorganisms and Cell Cultures (DSMZ) under accession No. DSM23035 and mutant strains derived thereof.

Thus, apart from the deposited strain mentioned above, the invention also pertains to mutants that have been derived from this strain, i.e. they have been obtained by using the deposited strain CHCC5366 as a starting material. The mutant strain may be derived from the deposited strain, e.g., by means of genetic engineering, radiation, UV light, chemical treatment and/or methods that induce changes in the genome. A mutant according to the invention will inhibit and/or prevent the growth of certain bacteria or fungi, preferably molds. It is preferred that the mutant has essentially at least 80% or more, at least 90% or more, at least 95% or more, or even up to 100% or more of the antifungal effect compared with its mother strain when determined, e.g., in an assay as described in Example 1 using one of the molds *P. brevicompactum, P. commune, A. versicolor, D. hansenii* or *P. crustosum* as a reference organism the growth of which is to be inhibited.

It is clear for the skilled person that by using the deposited strain as starting material, the skilled reader can by conventional mutagenesis or re-isolation techniques routinely obtain further mutants or derivatives thereof that retain the herein described relevant features and advantages. Accordingly, the term "mutant strains derived thereof" of the first aspect relates to mutant strains obtained by using the deposited strain as starting material.

A second aspect relates to an antifungal composition comprising at least one *Lactobacillus rhamnosus* strain according to the first aspect of the invention, preferably *Lactobacillus rhamnosus* strain CHCC5366.

When testing *Lactobacillus rhamnosus* strain CHCC5366 in combination with different *Lactobacillus paracasei* strains, it was unexpectedly found that these combinations were even better than either of the strains alone even when the total concentrations of cells were identical. In one embodiment, the invention relates to a combination of *Lactobacillus rhamnosus* CHCC5366 and *Lactobacillus paracasei* CHCC12777. In another embodiment, the invention relates to a combination of *Lactobacillus rhamnosus* CHCC5366 and *Lactobacillus paracasei* CHCC14676. These combinations seemed to be more efficient than the bench mark cultures HOLDBAC™ YM-B and HOLDBAC™ YM-C from Danisco, Denmark.

Accordingly, in a preferred embodiment the present invention relates to antimicrobial and more preferably antifungal compositions comprising *Lactobacillus rhamnosus* strain CHCC5366 that was deposited with the German Collection of Microorganisms and Cell Cultures (DSMZ) under accession No. DSM23035 or a mutant derived thereof and at least one *Lactobacillus paracasei* strain. Preferably, the at least one *Lactobacillus paracasei* strain is selected from the group consisting of *Lactobacillus paracasei* strain CHCC14676 with accession no. DSM25612, *Lactobacillus paracasei* strain CHCC12777 with accession no. DSM24651 and mutant strains derived from these deposited strains.

In one aspect the invention thus provides an antimicrobial and more preferably antifungal composition comprising *Lactobacillus rhamnosus* strain CHCC5366 or a mutant derived thereof and *Lactobacillus paracasei* strain CHCC12777 or a mutant derived thereof. In another aspect, the invention provides an antimicrobial and more preferably antifungal composition comprising at least *Lactobacillus rhamnosus* strain CHCC5366 or a mutant derived thereof and *Lactobacillus paracasei* strain CHCC14676 or a mutant derived thereof. Preferably, the combination of the *Lactobacillus paracasei* strain and the *Lactobacillus rhamnosus* strain in the compositions of the invention act synergistically in terms of their antimicrobial and/or antifungal activity.

The antifungal composition typically comprises the bacteria in a concentrated form including frozen, dried or freeze-dried concentrates typically having a concentration of viable cells, which is in the range of $10^4$ to $10^{12}$ cfu (colony forming units) per gram of the composition including at least $10^4$ cfu per gram of the composition, such as at least $10^5$ cfu/g, e. g. at least $10^6$ cfu/g, such as at least $10^2$ cfu/g, e.g. at least $10^8$ cfu/g, such as at least $10^9$ cfu/g, e.g. at least $10^{10}$ cfu/g, such as at least $10^{11}$ cfu/g. Thus, the composition of the invention is preferably present in a frozen, dried or freeze-dried form, e.g. as a Direct Vat Set (DVS) culture. However, as used herein the composition may also be a liquid that is obtained after suspension of the frozen, dried or freeze-dried cell concentrates in a liquid medium such as water or PBS buffer. Where the composition of the invention is a suspension, the concentration of viable cells is in the range of $10^4$ to $10^{12}$ cfu (colony forming units) per ml of the composition including at least $10^4$ cfu per ml of the composition, such as at least $10^5$ cfu/ml, e.g. at least $10^6$ cfu/ml, such as at least $10^2$ cfu/ml, e.g. at least $10^8$ cfu/ml, such as at least $10^9$ cfu/ml, e.g. at least $10^{10}$ cfu/ml, such as at least $10^{11}$ cfu/ml.

The composition may as further components contain cryoprotectants and/or conventional additives including nutrients such as yeast extracts, sugars and vitamins, e.g. vitamin A, C, D, K or vitamins of the vitamin B family. Suitable cryoprotectants that may be added to the compositions of the invention are components that improve the cold tolerance of the microorganisms, such as mannitol, sorbitol, sodium tripolyphosphate, xylitol, glycerol, raffinose, maltodextrin, erythritol, threitol, trehalose, glucose and fructose. Other additives may include, e.g., carbohydrates, flavors, minerals, enzymes (e.g. rennet, lactase and/or phospholipase).

In compositions of the invention which comprise *Lactobacillus rhamnosus* strain CHCC5366 strain and a *Lactobacillus paracasei* strain, the ratio between the *Lactobacillus rhamnosus* strain CHCC5366 and the *Lactobacillus paracasei* strain, e.g. the ratio of the concentration or number of *Lactobacillus rhamnosus* bacteria and the concentration or number of *Lactobacillus paracasei* bacteria, preferably amounts from 1:100 to 100:1, preferably 1:10 to 10:1.

The antifungal composition of the present invention may be used in connection with any food, feed and pharmaceutical product which is susceptible to microbial degradation and/or contamination with yeasts and molds. These include, but are not limited to fruits and vegetables including derived products, grain and grain derived products, dairy products, meat, poultry, and seafood. In particularly preferred embodiments, the composition is used in connection with dairy product and/or meat and poultry. In a preferred embodiment, the compositions of the invention are for use as an additive in the preparation of dairy products, such as yoghurt, tvarog, sour cream, cream cheese and the like.

In a preferred embodiment the compositions of the invention are used against fungi, such as yeasts and molds. This means that the compositions are used for inhibiting and/or preventing the growth of fungi which cause contamination in dairy industry processes, in particular milk fermentation processes. The compositions of the present invention can be used, e.g., for inhibiting and/or preventing the growth of yeasts, such as yeasts of the genera *Klyveromyces* (e.g., *K. marxianus, K. lactis*), *Pichia* (e.g., *P. fermentans*), *Yarrowia* (e.g., *Y. lipolytica*), *Candida* (e.g., *C. sake*), and the like; or molds, such as molds from the genera *Penicillium* (e.g., *P. nalgiovense, P. commune, P. crustosum, P. brevicompactum, P. glabrum*), *Mucor* spp., *Cladiosporium* ssp., *Aspergillus* (e.g., *A. versicolor*), *Debaryomyces* (e.g., *D. hansenii*), and the like. It is especially preferred to use the compositions of the invention to inhibit and/or prevent growth of the species *Klyveromyces marxianus, Yarrowia lipolytica, Penicillium nalgiovense, Cladiosporium* ssp., *Penicillium commune, Mucor* ssp., *Penicillium brevicompactum, Aspergillus versicolor, Penicillium crustosum, Kluyveromyces lactis*, and/or *Debaryomyces hansenii*.

The antifungal composition according to the second aspect of the present invention may also be used as a pharmaceutical product, preferably one for treating infections with pathogenic fungi, such as pathogenic yeasts.

In a third aspect, the present invention is directed to a food, feed or pharmaceutical product comprising a *Lactobacillus rhamnosus* strain according to the first aspect of the invention or an antifungal composition according to the second aspect of the invention.

In a preferred embodiment the food, feed or pharmaceutical product is a food product.

In a more preferred embodiment such a food product is selected from the group consisting of fruits and fruit derived products, vegetable and vegetable derived products, grain and grain derived products, dairy products, meat, poultry and seafood and mixtures thereof.

In an even more preferred embodiment the food product is a dairy product, preferably a mesophilic or a thermophilic fermented milk product, such as fresh cheese, a yoghurt, a sour cream or tvarog.

In another preferred embodiment the food product is meat or poultry.

In a preferred embodiment the food, feed or pharmaceutical product is a pharmaceutical product.

Preferably, the pharmaceutical product is a product useful for administration of the antifungal composition according to a second aspect of the present invention to a human or an animal to inhibit pathogenic microorganisms and alleviating symptoms related to the pathogenic microorganisms. Examples of such symptoms include symptoms related to yeast infection. In such an embodiment, the pharmaceutical product may be a unit dosage form comprising the antifungal composition. Preferably, the unit dosage form is a capsule or a tablet. However, the unit dosage form may also be suitable for application to the mucosa or skin and, thus, be in the form of a paste, cream, ointment and the like.

A fourth aspect of the present invention relates to a method for manufacturing a food, feed or pharmaceutical product according to the third aspect of the present invention comprising adding at least one *Lactobacillus rhamnosus* strain according to the first aspect or an antifungal composition according to the second aspect of the invention during the manufacture of the food, feed or pharmaceutical product. Preferably, the method also comprises the step of controlling the manufacturing parameters during the manufacturing such that the concentration of the at least one *Lactobacillus rhamnosus* strain remains constant or is increased.

In a preferred embodiment the concentration of the at least one strain of *Lactobacillus rhamnosus* is at least $1\times10^6$ cfu/g or each at least $1\times10^6$ cfu/ml of the food, feed or pharmaceutical product, or each at least $1\times10^5$ cfu/cm$^2$ of the surface of the food, feed or pharmaceutical product. Preferably, the concentration of the at least one strain of *Lactobacillus rhamnosus* is at least $5\times10^6$ cfu/g or each at least $5\times10^6$ cfu/ml of the food, feed or pharmaceutical product, or each at least $5\times10^5$ cfu/cm$^2$ of the surface of the food, feed or pharmaceutical product, such as at least $1\times10^2$ cfu/g or each at least $1\times10^2$ cfu/ml of the food, feed or pharmaceutical product, or each at least $1\times10^6$ cfu/cm$^2$ of the surface of the food, feed or pharmaceutical product, such as at least $5\times10^7$ cfu/g or each at least $5\times10^7$ cfu/ml of the food, feed or pharmaceutical product, or each at least $5\times10^6$ cfu/cm$^2$ of the surface of the food, feed or pharmaceutical product.

Where the food, feed or pharmaceutical product is manufactured by addition of a composition comprising *Lactobacillus rhamnosus* strain CHCC5366 or a mutant derived thereof and at least one strain of *Lactobacillus paracasei*, the concentration of *Lactobacillus rhamnosus* strain CHCC5366 or the mutant derived thereof and/or the concentration of the at least one strain of *Lactobacillus paracasei* is each at least $1\times10^6$ cfu/g or each at least $1\times10^6$ cfu/ml of the food, feed or pharmaceutical product, or each at least $1\times10^5$ cfu/cm$^2$ of the surface of the food, feed or pharmaceutical product. Preferably, the concentration of *Lactobacillus rhamnosus* strain CHCC5366 or the mutant derived thereof and/or the concentration of the at least one strain of *Lactobacillus paracasei* is each at least $5\times10^6$ cfu/g or each at least $5\times10^6$ cfu/ml of the food, feed or pharmaceutical product, or each at least $5\times10^5$ cfu/cm$^2$ of the surface of the food, feed or pharmaceutical product. In a further embodiment, the concentration of *Lactobacillus rhamnosus* strain CHCC5366 or the mutant derived thereof and/or the concentration of the at least one strain of *Lactobacillus paracasei* is each at least $1\times10^8$ cfu/g or each at least $1\times10^8$ cfu/ml of the food, feed or pharmaceutical product, or each at least $1\times10^7$ cfu/cm$^2$ of the surface of the food, feed or pharmaceutical product.

In a preferred embodiment, the manufacturing parameters are controlled during the manufacturing such that the concentration of *Lactobacillus rhamnosus* strain CHCC5366 (or the mutant derived thereof) and the at least one strain of *Lactobacillus paracasei* increases or remains constant.

An antifungal composition according to the present invention is most readily used by mixing with and/or applying on a blendable food, feed or pharmaceutical product, but should also be effective to treat the surface of solid food products, or the interior of such products, e.g. by injection. In still other embodiments, the composition may be applied as a marinade, breading, seasoning rub, glaze, colorant mixture, and the like, the key criteria being that the antifungal composition be available to the surface subject to bacterial degradation and contamination with yeasts and molds. In still other embodiments, the composition may be indirectly placed into contact with the food surface by applying the composition to food packaging and thereafter applying the packaging to the food surface. The optimum amount to be used will depend on the composition of the particular food product to be treated and the method used for applying the composition to the food surface, but can be determined by simple experimentation.

In a much preferred embodiment the method comprises one or more fermentation steps and the at least one *Lactobacillus rhamnosus* strain or the antifungal composition may be added to the food, feed or pharmaceutical product prior to, during or after such one or more fermentation steps.

Preferably, the method comprises the fermentation of a substrate, such as a milk substrate, in the presence of at least one *Lactobacillus rhamnosus* strain according to the invention for a period of time sufficient for the appearance of antifungal activity of the at least one *Lactobacillus rhamnosus* strain according to the invention. This antifungal activity has the effect of inhibiting the development of yeasts and/or molds in the product fermented with the at least one strain.

In an even more preferred embodiment the method comprises fermenting a milk substrate with a starter culture comprising at least one strain of the genera selected from *Lactobacillus, Streptococcus, Lactococcus* and *Leuconostoc*, such as at least one strain of *Lactobacillus bulgaricus* and at least one strain of *Streptococcus thermophilus* or such as at least one strain of *Lactococcus lactis* subsp. *lactis*, at least one strain of *Leuconostoc mesenteroides* subsp. *cremoris* and at least one strain of *Lactococcus lactis* subsp. *diacetylactis*.

The fifth aspect of the invention relates to a food product obtainable by the method according the fourth aspect of the invention.

The sixth aspect of the present invention is directed to use of a *Lactobacillus rhamnosus* strain according to the first aspect or an antifungal composition according to the second aspect for preparing a food, feed or pharmaceutical product. Preferably, the food product produced by use of the *Lactobacillus paracasei* strain according to the first aspect or the antifungal composition according to the second aspect is a cheese, such as a Cottage, Feta, Cheddar, Parmesan, Mozzarella, Emmentaler, Danbo, Gouda, Edam, Feta-type, blue cheese, brine cheese, Camembert or Brie.

The last aspect of the invention relates to use of a *Lactobacillus rhamnosus* strain according the first aspect or an antifungal composition according to the second aspect for inhibiting the growth of yeasts and molds, in particular in food and feed products.

Embodiments of the present invention are described below, by way of non-limiting examples.

EXAMPLES

Example 1

Challenge Study on Yoghurt with *Lactobacillus rhamnosus* CHCC5366

For the visual examination of the inhibitory effect of *Lactobacillus rhamnosus* strain CHCC5366 on the different molds, *P. brevicompactum, P. commune, A. versicolor* and *P. crustosum*, yoghurt with 1.5% fat was prepared:

Homogenized milk (1.5% fat) was heat-treated 95° C.±1° C. for 5 min. in 1 L bottles in a water bath and cooled immediately. A commercial starter culture (F-DVS YF-L901 obtainable from Chr. Hansen A/S, Denmark) was inoculated at 0.02%. The milk was further inoculated with HOLDBAC™ YM-B (20 DCU/100 L) or *Lactobacillus rhamnosus* CHCC5366 (1×10$^7$ CFU/ml) and one bottle was used as reference and only inoculated with starter culture.

The milk was fermented at 43° C.±1° C. until pH of 4.60±0.1 was reached. The resulting yoghurt was poured into cups (100 g) and stored at 7° C.±1° C.

One day after preparation of yoghurt different molds were inoculated as surface contaminants in duplicate cups of yoghurt with one spot on the surface of the yoghurt with a target of 100 spores/spot. Growth of the molds were assessed visually after storage for 45 days at 7° C.±1° C.

The result of the yoghurt test is presented in FIG. 1, showing that *P. brevicompactum* (M1), *P. commune* (M6), *A. versicolor* (M7) and *P. crustosum* (M10) grow well on yoghurt made from milk fermented only with the starter culture YF-L901 (top row) or with the starter culture and the HOLDBAC™ YM-B culture (middle row). In contrast, when *Lactobacillus rhamnosus* CHCC5366 was present during milk fermentation (bottom row) the growth of all tested molds was inhibited.

Example 2

Quantitative Determinations of the Inhibitory Effect of *Lactobacillus rhamnosus* CHCC5366 Against *Debaryomyces hansenii*

For a quantitative examination of the inhibitory effect of *Lactobacillus rhamnosus* CHCC5366 on *D. hansenii*, yoghurt was prepared:

Homogenized milk (1.5% fat) was heat-treated at 95° C.±1° C. for 5 min. in 1 L bottles in a water bath. The milk was cooled immediately. Each bottle was inoculated with a commercial starter culture (F-DVS YF-L901 obtainable from Chr. Hansen A/S, Denmark) at 0.02%. The milk was further inoculated with HOLDBAC™ YM-B (20 DCU/100 L) or HOLDBAC™ YM-C (10 DCU/100 L) or *Lactobacillus rhamnosus* CHCC5366 (1×10$^7$ CFU/g) and one bottle was used as reference and only inoculated with starter culture.

The milk was fermented at 43° C.±1° C. until pH of 4.60±0.05 was reached. The resulting yoghurt was poured into cups (approx. 75 ml) and stored at 7° C.±1° C.

The day after preparing the yoghurt, the cups were inoculated in duplicate with 0.75 ml/cup of yeast at a target of 20 CFU/g. The yeast was equally dispersed in the yoghurt. The cups were stored under lid at 7° C.±1° C. and analyzed at suitable intervals for the *D. hansenii* contamination level by plating 1 ml of yoghurt and further appropriate 1-fold dilutions made in saline peptone on Yeast Glucose Chloramphenicol (YGC) agar followed by aerobic incubation for 5 days at 25° C.

Figure 2:
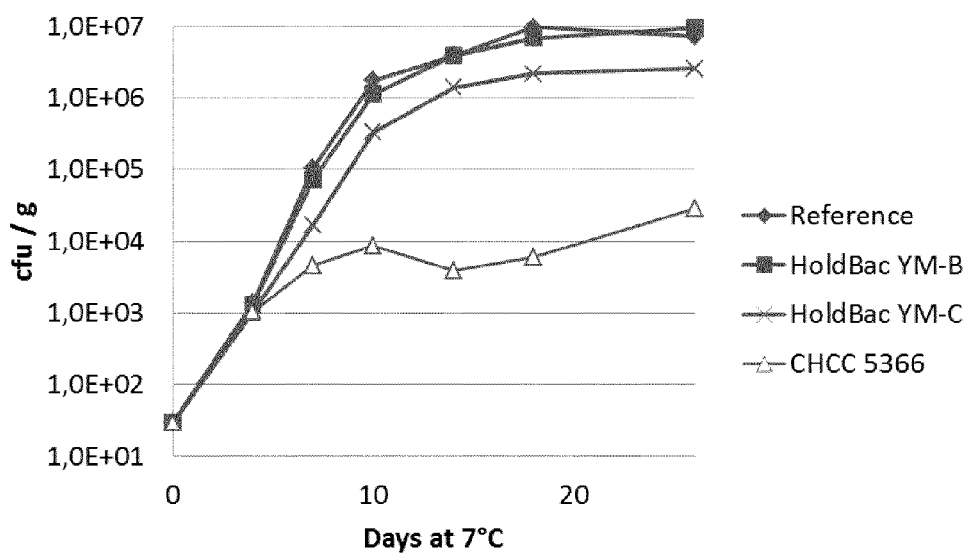
FIG. 2 depicts cell counts of a *Debaryomyces hansenii* isolate added to yoghurt with 1.5% fat fermented with a starter culture YF-L901 alone (Reference) or together with the following strains: HOLDBAC™ YM-B (HoldBac YM-B), HOLDBAC™ YM-C (HoldBac YM-C) or *Lactobacillus rhamnosus* CHCC5366 (CHCC 5366). Yoghurts were stored at 7±1° C. and analyzed at suitable intervals.

As illustrated in FIG. 2, growth of *D. hansenii* was inhibited in the presence of *Lactobacillus rhamnosus* strain CHCC5366 when inoculated together with the starter culture YF-L901 before fermentation. The strain caused significantly higher inhibition than the commercial cultures, HOLDBAC™ YM-B and HOLDBAC™ YM-C.

Example 3

Semi-Quantitative Determinations of the Inhibitory Effect of *Lb. Paracasei* CHCC14676 and *Lb. rhamnosus* CHCC5366 Alone and in Combination Against Different Mold Contaminants For the semi-quantitative examinations of *Lb. paracasei* CHCC14676 and *Lb. rhamnosus* CHCC5366 alone and in combination, an agar-assay was used, resembling the manufacturing process and product of yoghurt:

Homogenized milk (1.5% fat w/v) was heat-treated at 95° C. for five minutes and cooled immediately. A commercial starter culture (F-DVS YC-350 obtainable from Chr. Hansen A/S, Denmark) was inoculated at 0.02%, and the milk was distributed to 220 ml bottles. The bottles were further inoculated with *Lb. paracasei* CHCC14676, *Lb. rhamnosus* CHCC5366 and a combination of the two strains, respectively, in total concentrations of 1×10$^7$ CFU/ml. One bottle without further inoculation than starter culture was used as reference. Furthermore, 5% of a pH-indicator of bromcresol purple and bromcresol green was added to all bottles to get an indication of the speed of acidification, and to obtain a blue/green color of the media which would make subsequent growth of target yeasts and molds more easily detectable. All bottles were incubated in a water bath at 43±1° C. and fermented at these conditions until pH of 4.60±0.1 was reached. After fermentation, the bottles were immediately cooled on ice and vigorously shaken to break the coagulum. Then the fermented milk was warmed to a temperature of 40° C. and added to 40 ml of a 5% sterile agar solution that had been melted and cooled down to 60° C. This solution was then poured into sterile Petri dishes and the plates were dried in a LAF bench for 30 min.

Fully outgrown spore suspensions in appropriate dilutions of the selected molds *Penicillium nalgiovense* (10×), *Penicillium commune* (100×), *Aspergillus versicolor* (100×) and *Penicillium crustosum* (100×) were spotted on the plates. The plates were incubated at 7° C. and examined for the growth of mold at suitable, regular intervals.

Figure 3:
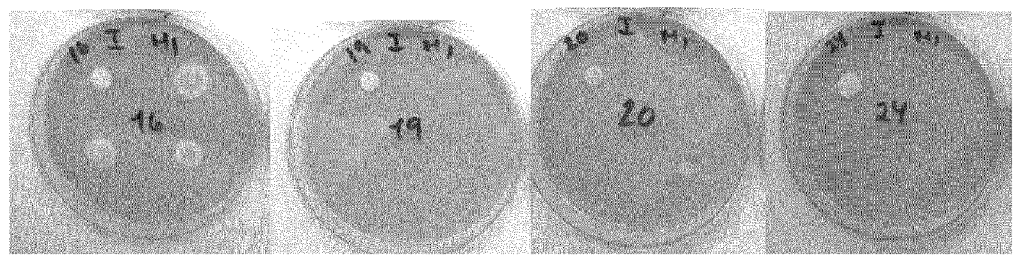
FIG. 3 shows growth of molds on plates prepared from milk fermented with a starter culture alone (reference, first picture), together with *Lb. paracasei* CHCC14676 (second picture), together with *Lb. rhamnosus* CHCC5366 (third picture) or together with a combination of *Lb. paracasei* CHCC14676 and *Lb. rhamnosus* CHCC5366 (fourth picture). The target contaminants were added in the concentrations mentioned in the text from top left and moving clock-wise to the bottom left of the plate: *Penicillium nalgiovense, Penicillium commune, Aspergillus versicolor* and *Penicillium crustosum*, respectively. The plates had been incubated at 7±1° C. for 12 days.

Results of the agar-assay are presented in FIG. 3, showing that all of the tested molds grew very well on the agar plates from milk fermented only with the starter culture (reference). However, when *Lb. paracasei* CHCC14676 or *Lb. rhamnosus* CHCC5366 were present during milk fermentation, the resulting plates strongly reduced growth of all molds. Furthermore, when *Lb. paracasei* CHCC14676 and *Lb. rhamnosus* CHCC5366 were present in combination during milk fermentation, even stronger inhibition was observed for *Penicillium commune, Aspergillus versicolor* and *Penicillium crustosum* spotted on the plates.

Example 4

Challenge Study with *Lb. Rhamnosus* CHCC5366 and Potassium Sorbate

Pasteurized milk containing 0.17% fat was used to prepare three different batches of yoghurt using the commercial starter culture referred to in Example 1. The starter culture was inoculated at 0.013%. Prior to fermentation, potassium sorbate (0.023%) was added to the first batch, *Lactobacillus rhamnosus* CHCC5366 ($1 \times 10^7$ CFU/g) was added to the second batch, while the third batch was used as a reference containing only the starter culture. Fermentation was carried out at 43° C. until a pH of 4.55 was reached. After reaching pH 4.55, the yoghurt was stored at 7° C.

The three different types of yoghurt were distributed into small cups with approx. 100 g in each and surface inoculated with each of the following molds previously isolated from spoiled fermented milk products to reach a target inoculation of approx. 1000 spores/cup:
Penicillium solitum,
Penicillium palitans,
Penicillium discolor,
Penicillium spathulatum,
Penicillium commune,
Penicillium crustosum,
Penicillium paneum,
Penicillium roqueforti, The yoghurts were incubated at 7° C. for 60 days, and the outgrowth of the different molds was visually monitored by taking pictures at the end of the 60-days period.

Figure 4:
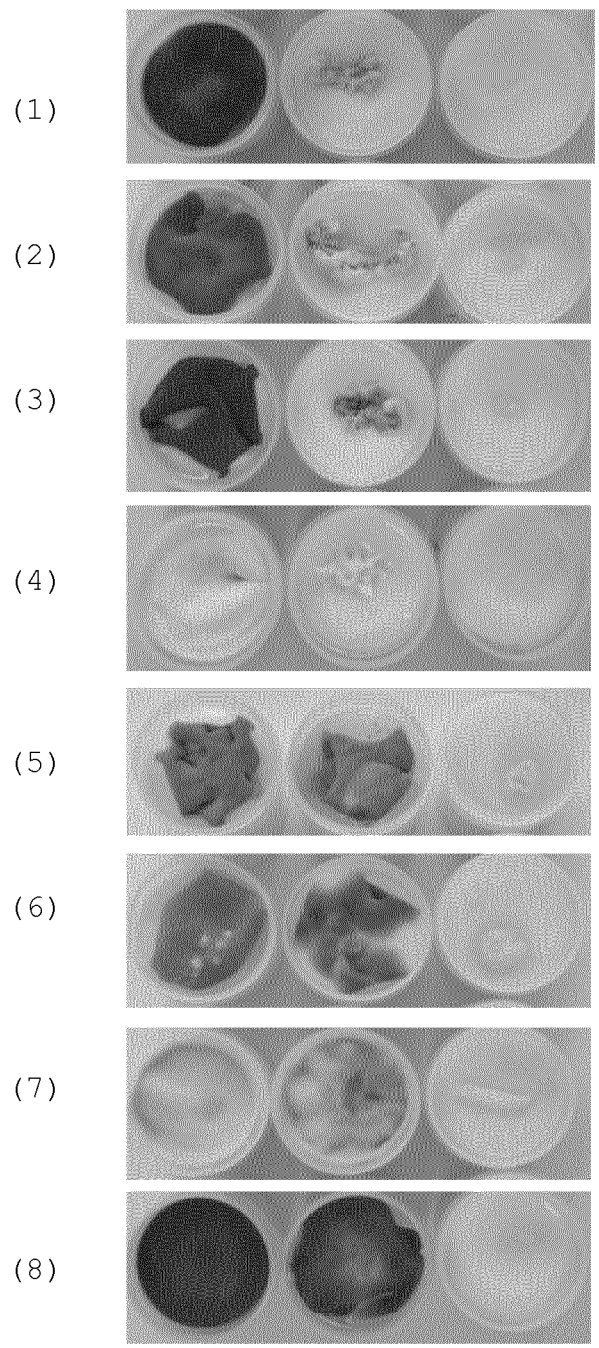
FIG. 4 shows the growth of: (1) *Penicillium solitum*, (2) *P. palitans*, (3) *P. discolor*, (4) *P. spathulatum*, (5) *P. commune*, (6). *P. crustosum*, (7) *P. paneum*, (8) *P. roqueforti* in a reference yoghurt (left column), a yoghurt made with 0.023% potassium sorbate (middle column) and a yoghurt made with 1E+07 cfu/g of CHCC5366 (right column) after 60 days incubation at 7° C. when inoculated in concentrations of approx. 1000 spores/cup.

The results presented in FIG. 4 demonstrate that the presence of *Lactobacillus rhamnosus* CHCC5366 dramatically reduced the outgrowth and the formation of the typical green/blue color of the various molds in the yoghurt during 60 days storage at 7° C. The inhibitory effect of *Lactobacillus rhamnosus* CHCC5366 on the extent of outgrowth and color formation of the molds was found to be considerably stronger than the effect exerted by the addition of 0.023% potassium sorbate.

Example 5

Challenge Study on Greek Yoghurt with *Lactobacillus rhamnosus* CHCC5366 and *Lactobacillus paracasei* CHCC14676 in Combination For the visual examination of the inhibitory effect of *Lactobacillus rhamnosus* CHCC5366 and *Lactobacillus paracasei* CHCC14676 in combination on *Mucor* ssp. Greek yoghurt was prepared substantially as follows:

Pasteurized 1.5% fat milk was inoculated with a commercial starter culture (F-DVS YF-L901 obtainable from Chr. Hansen A/S, Denmark) at 0.02%. One batch only inoculated with starter culture was used as a reference. Another batch was further inoculated with a combination of *Lactobacillus rhamnosus* strain CHCC5366 ($5 \times 10^6$ CFU/g) and *Lactobacillus paracasei* strain CHCC14676 ($5 \times 10^6$ CFU/g).

The milk was fermented at 43° C.±1° C. to a final pH of 4.55 (6-7 hours). Subsequently, the yoghurt was cooled to 25° C.±1° C. with a back pressure of 2 bars and stored at 6° C.±1° C.

One day after preparation of the yoghurt, *Mucor* ssp. was inoculated as surface contaminant in duplicate cups of yoghurt by applying one spot on the surface of the yoghurt with a target inoculation concentration of 100 spores/spot. The growth of the mold was assessed visually after storage for 15 days at 22° C.±1° C.

Figure 5:
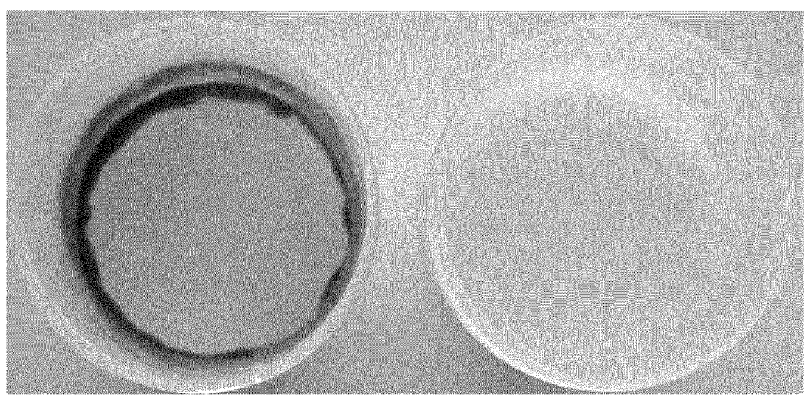
FIG. 5 shows growth of *Mucor* ssp. on Greek yoghurt prepared from milk fermented with a starter culture only (left cup) or from milk fermented in the presence of *Lactobacillus rhamnosus* CHCC5366 and *Lactobacillus paracasei* CHCC14676 (right cup).

The results of the Greek yoghurt test are presented in FIG. 5, showing that *Mucor* ssp. grows well on the yoghurt made from milk fermented only with the starter culture (left cup). In contrast, when *Lactobacillus rhamnosus* CHCC5366 and *Lactobacillus paracasei* CHCC14676 were present during milk fermentation (right cup) the growth of *Mucor* ssp. was inhibited.

Example 6

Second Challenge Study on Greek Yoghurt with a Combination of *Lactobacillus rhamnosus* CHCC5366 and *Lactobacillus paracasei* CHCC14676

For the visual examination of the inhibitory effect of the combination of *Lactobacillus rhamnosus* CHCC5366 and *Lactobacillus paracasei* CHCC14676 on the black bread mold *Rhizopus stolonifer* the Greek yoghurt was prepared substantially as follows:

Pasteurized 1.5% fat milk was inoculated with a commercial starter culture (F-DVS YF-L901 obtainable from Chr. Hansen A/S, Denmark) at 0.02%. The milk was further inoculated with HOLDBAC™ YM-B (10 DCU/100 l), with *Lactobacillus rhamnosus* strain CHCC5366 ($1 \times 10^7$ CFU/g), or with a combination of *Lactobacillus rhamnosus* strain CHCC5366 ($5 \times 10^6$ CFU/g) and *Lactobacillus paracasei* strain CHCC14676 ($5 \times 10^6$ CFU/g). One batch was used as reference and only inoculated with starter culture.

The milk was fermented at 43° C.±1° C. to a final pH of 4.55 (6-7 hours). Subsequently, the yoghurt was cooled to 25° C.±1° C. with a back pressure of 2 bars and stored at 6° C.±1° C.

One day after preparation of the yoghurt, *Rhizopus stolonifer* was inoculated as a surface contaminant in duplicate cups of yoghurt by applying one spot on the surface of the yoghurt with a target contamination of 100 spores/spot. Growth of the mold was assessed visually after storage for 42 days at 7° C.±1° C.

Figure 6:
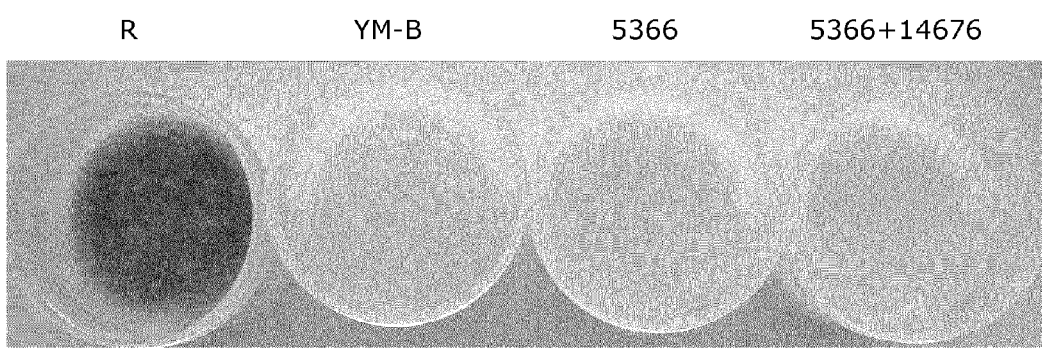
FIG. 6 shows growth of the mold *Rhizopus stolonifer* on Greek yoghurt prepared from milk fermented with a starter culture only (R, i.e. reference), with the starter culture and HOLDBAC™ YM-B (YM-B), with the starter culture and *Lactobacillus rhamnosus* CHCC5366 (5366), or with the starter culture and a combination of *Lactobacillus rhamnosus* CHCC5366 and *Lactobacillus paracasei* CHCC14676 (5366+14676).

The result of the Greek yoghurt test is presented in FIG. 6, showing that *Rhizopus stolonifer* grows well on the yoghurt made from milk fermented only with the starter culture ("R", i.e. reference) or with the starter culture and the HOLDBAC™ YM-B culture (YM-B). However, when *Lactobacillus rhamnosus* CHCC5366 (5366) was present, the growth of *Rhizopus stolonifer* was inhibited significantly. When *Lactobacillus rhamnosus* CHCC5366 and *Lactobacillus paracasei* CHCC14676 were both present during milk fermentation (5366+14676) the growth of *Rhizopus stolonifer* was inhibited almost completely.

Example 7

Challenge Study on White Brine Cheese with *Lactobacillus rhamnosus* CHCC5366 and *Lactobacillus paracasei* CHCC14676 in Combination For the quantitative examination of the inhibitory effect of *Lactobacillus rhamnosus* CHCC5366 and *Lactobacillus paracasei* CHCC14676 in combination against *Saccharomyces cerevisiae*, white brine cheese was prepared:

Pasteurized and standardised milk was inoculated with a commercial starter culture (FD-DVS SafeIT-1 obtainable from Chr. Hansen A/S, Denmark) at 40 U per 1000 l milk. The milk was further inoculated with HOLDBAC™ YM-B (10 DCU/100 l) or with a combination of *Lactobacillus rhamnosus* strain CHCC5366 (5×10$^6$ CFU/g) and *Lactobacillus paracasei* strain CHCC14676 (5×10$^6$ CFU/g). One batch was used as reference and only inoculated with starter culture. The milk was rennet-treated at 36° C.±1° C. using Chy-Max plus (obtained from Chr. Hansen A/S, Denmark) with 220 ml per 1000 l for 90 min. before cutting. At pH 6.0 the curd was pumped to the molds and left for drainage to a final pH of 4.8-4.7 (20-24 hours). The cheeses were added into tins with cold brine (8%) and stored at 5° C.±1° C.

One day after preparation of the white brine cheese, the tins were inoculated in duplicate with yeast at a target of 20 CFU/ml. The yeast was equally dispersed in the brine. The cups were stored under lid at 7° C.±1° C. for up to 40 days and 10 g were analysed at suitable intervals for the *Saccharomyces cerevisiae* contamination level by plating appropriate 1-fold dilutions made in saline peptone on Yeast Glucose Chloramphenicol (YGC) agar followed by aerobic incubation for 5 days at 25° C.

Figure 7:
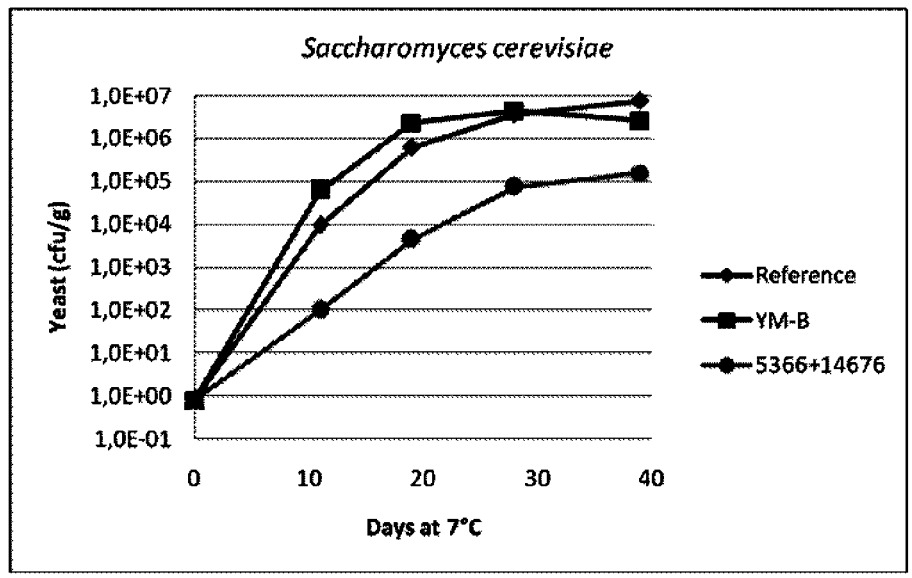
FIG. 7 shows growth of *Saccharomyces cerevisiae* on white brine cheese made from milk fermented only with starter culture (reference); with starter culture and HOLD- BAC™ YM-B (YM-B); or with starter culture, *Lactobacillus paracasei* CHCC14676 and *Lactobacillus rhamnosus* CHCC5366 (5366+14676).

As illustrated in FIG. 7, growth of *Saccharomyces cerevisiae* was inhibited in the presence of *Lactobacillus rhamnosus* CHCC5366 and *Lactobacillus paracasei* CHCC14676 in combination when inoculated together with the starter culture SafeIT-1. The strains caused significantly higher inhibition than the commercially available culture, HOLDBAC™ YM-B.

Example 8

Second Challenge Study on White Brine Cheese with *Lactobacillus rhamnosus* CHCC5366 and *Lactobacillus paracasei* CHCC14676 in Combination For the quantitative examination of the inhibitory effect of *Lactobacillus rhamnosus* CHCC5366 and *Lactobacillus paracasei* CHCC14676 in combination against *Kluyveromyces marxianus*, white brine cheese was prepared as described in example 1, with the exception that the tins were inoculated with *Kluyveromyces marxianus* as yeast contaminant.

Figure 8:
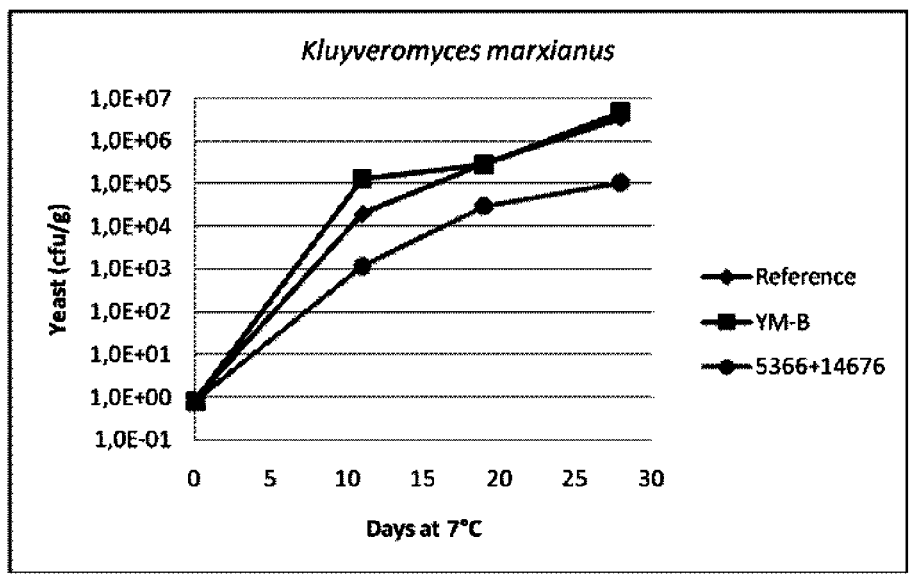
FIG. 8 shows growth of *Kluyveromyces marxianus* on white brine cheese made from milk fermented only with starter culture (reference); with starter culture and HOLDBAC™ YM-B (YM-B); or with starter culture, *Lactobacillus paracasei* CHCC14676 and *Lactobacillus rhamnosus* CHCC5366 (5366+14676).

As illustrated in FIG. 8, growth of *Kluyveromyces marxianus* was inhibited in the presence of *Lactobacillus rhamnosus* CHCC5366 and *Lactobacillus paracasei* CHCC14676 in combination when inoculated together with the starter culture SafeIT-1. The strains caused significantly higher inhibition than the commercially available culture HOLDBAC™ YM-B.

Example 9

Third Challenge Study on White Brine Cheese with *Lactobacillus rhamnosus* CHCC5366 and *Lactobacillus paracasei* CHCC14676 in Combination For the visual examination of the inhibitory effect of *Lactobacillus rhamnosus* CHCC5366 and *Lactobacillus paracasei* CHCC14676 in combination against *P. commune*, white brine cheese was prepared as described in example 1.

7 days after preparation of the white brine cheese, the cheese was removed from the brine and *P. commune* was inoculated as surface contaminant on duplicate cheeses with three spots on the surface of the cheese with a target of 100 spores/spot. Growth of two different *P. commune* isolates were assessed visually after storage for 12 days at 7° C.±1° C. and, subsequently, 16 days at 12° C.±1° C.

Figure 9:
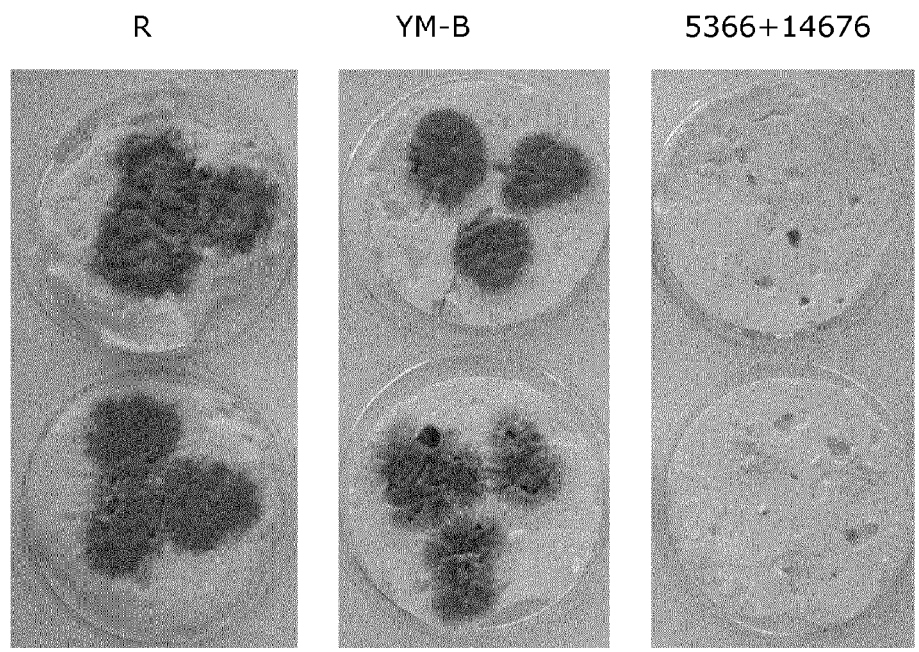
FIG. 9 shows growth of *Penicillium commune* on white brine cheese made from milk fermented only with starter culture (R, i.e. reference); with starter culture and HOLDBAC™ YM-B (YM-B); or with starter culture, *Lactobacillus paracasei* CHCC14676 and *Lactobacillus rhamnosus* CHCC5366 (5366+14676).

The results of the white brine test are presented in FIG. 9, showing that the two *P. commune* isolates grow-well on the white brine cheese made from milk inoculated only with the starter culture (left). In contrast, when *Lactobacillus rhamnosus* CHCC5366 and *Lactobacillus paracasei* CHCC14676 were present during cheese production (right) the growth of *P. commune* was strongly inhibited.

Example 10

Challenge Study on White Brine Cheese with *Lactobacillus paracasei* CHCC5366

For the visual examination of the inhibitory effect of *Lactobacillus rhamnosus* CHCC5366 against *P. crustosum*, white brine cheese was prepared:

Pasteurized and standardised milk was inoculated with a commercial starter culture (FD-DVS SafeIT-1 obtainable from Chr. Hansen A/S, Denmark) at 40 U per 1000 l milk. The milk was further inoculated with HOLDBAC™ YM-B (10 DCU/100 l) or *Lactobacillus rhamnosus* strain CHCC5366 (1×10$^7$ CFU/g). One batch was used as reference and only inoculated with starter culture. The milk was rennet-treated at 36° C.±1° C. using Chy-Max plus (obtained from Chr. Hansen A/S, Denmark) with 220 ml per 1000 l for 90 min. before cutting. At pH 6.0 the curd was pumped to the molds and left for drainage to a final pH of 4.8-4.7 (20-24 hours). The cheeses were added into tins with cold brine (8%) and stored at 5° C.±1° C.

7 days after preparation of the white brine cheese, the cheese was removed from the brine and *P. crustosum* was inoculated as surface contaminant on duplicate cheeses with three spot on the surface of the cheese with a target of 100 spores/spot. Growth of the *P. crustosum* isolate was assessed visually after storage for 11 days at 12° C.±1° C., and, subsequently, 16 days at 12° C.±1° C.

Figure 10:
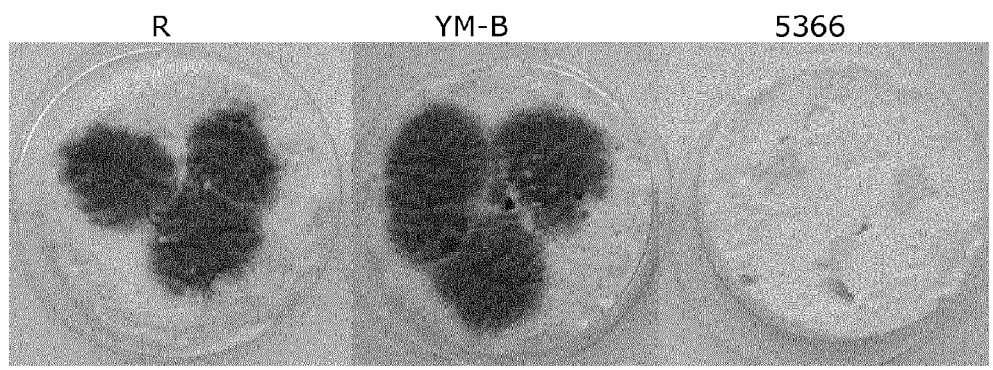
FIG. 10 shows growth of *P. crustosum* on white brine cheese made from milk fermented only with starter culture (R, i.e. reference); with starter culture and HOLDBAC™ YM-B (YM-B); or with starter culture and *Lactobacillus rhamnosus* CHCC5366 (5366).

The results of the white brine test are presented in FIG. 10 showing that the P. crustosum isolate grow well on the white brine cheese made from milk inoculated only with the starter culture (left). In contrast, when Lactobacillus rhamnosus CHCC5366 was present during cheese production (right) the growth of P. crustosum was inhibited.

Example 11

Challenge Study on Yoghurt with Lactobacillus rhamnosus CHCC5366 and CHCC14676 Against Penicillium paneum For the visual examination of the inhibitory effect of Lactobacillus rhamnosus strain CHCC5366 alone or in combination with Lactobacillus paracasei CHCC14676 on the mold P. paneum, yoghurt with 1.5% fat was prepared:

Homogenized milk (1.5% fat) was heat-treated 95° C.±1° C. for 5 min. in 1 L bottles in a water bath and cooled immediately. A commercial starter culture (F-DVS YF-L901 obtainable from Chr. Hansen A/S, Denmark) was inoculated at 0.02%. The milk was further inoculated with HOLDBAC™ YM-B (20 DCU/100 L), with Lactobacillus rhamnosus CHCC5366 ($1 \times 10^7$ CFU/ml) alone, or with a combination of Lactobacillus rhamnosus CHCC5366 ($5 \times 10^6$ CFU/ml) and Lactobacillus paracasei CHCC14676 ($5 \times 10^6$ CFU/ml). One bottle was used as reference and only inoculated with starter culture.

The milk was fermented at 43° C.±1° C. until pH of 4.60±0.1 was reached. The resulting yoghurt was poured into cups (100 g) and stored at 7° C.±1° C.

One day after preparation of yoghurt different molds were inoculated as surface contaminants in duplicate cups of yoghurt with one spot on the surface of the yoghurt with a target of 100 spores/spot. Growth of the molds were assessed visually after storage for 28 days at 7° C.±1° C.

Figure 11:
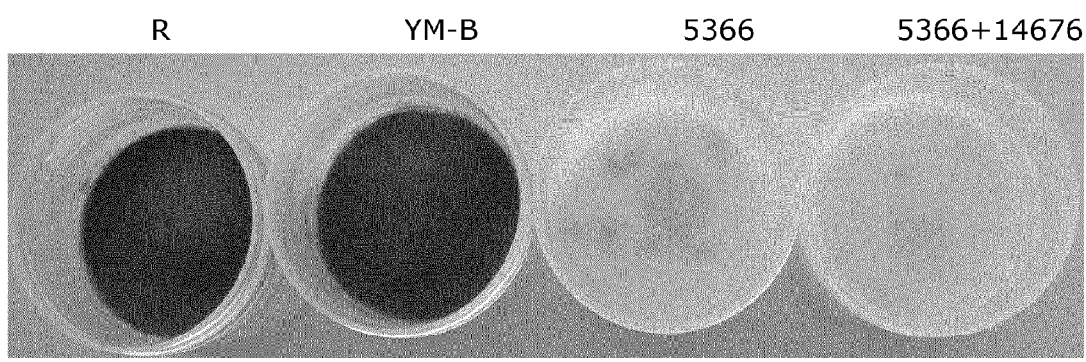
FIG. 11 depicts growth of the mold *Penicillium paneum* in yoghurt with 1.5% fat prepared from milk fermented with a starter culture alone (R, i.e. reference), with the starter culture and HOLDBAC™ YM-B (YM-B), with the starter culture and *Lactobacillus rhamnosus* CHCC5366 (5366), or with the starter culture and a combination of *Lactobacillus rhamnosus* CHCC5366 and *Lactobacillus paracasei* CHCC14676 (5366+14676).

The result of the yoghurt test is presented in FIG. 11, showing that P. paneum grows well on yoghurt made from milk fermented only with the starter culture YF-L901 or with the starter culture and the HOLDBAC™ YM-B culture. In contrast, when Lactobacillus rhamnosus CHCC5366 was present during milk fermentation the growth of P. paneum was strongly reduced, and the combination of Lactobacillus rhamnosus CHCC5366 and Lactobacillus paracasei CHCC14676 caused even stronger growth inhibition of P. paneum.

Example 12

Challenge Study on Yoghurt with Lactobacillus rhamnosus CHCC5366 and CHCC14676 at Different Storage Temperatures For the visual examination of the inhibitory effect of Lactobacillus rhamnosus strain CHCC5366 alone or in combination with Lactobacillus paracasei CHCC14676 on the mold P. crustosum at different storage temperatures, yoghurt with 1.5% fat was prepared:

Homogenized milk (1.5% fat) was heat-treated 95° C.±1° C. for 5 min. in 1 L bottles in a water bath and cooled immediately. A commercial starter culture (F-DVS YF-L901 obtainable from Chr. Hansen A/S, Denmark) was inoculated at 0.02%. The milk was further inoculated with HOLDBAC™ YM-B (20 DCU/100 L), with Lactobacillus rhamnosus CHCC5366 ($1 \times 10^7$ CFU/ml) alone, or with a combination of Lactobacillus rhamnosus CHCC5366 ($5 \times 10^6$ CFU/ml) and Lactobacillus paracasei CHCC14676 ($5 \times 10^6$ CFU/ml). One bottle was used as reference and only inoculated with starter culture.

The milk was fermented at 43° C.±1° C. until pH of 4.60±0.1 was reached. The resulting yoghurt was poured into cups (100 g) and stored at 7° C.±1° C.

One day after preparation of yoghurt Penicillium crustosum was inoculated as surface contaminant in duplicate cups of yoghurt with one spot on the surface of the yoghurt with a target of 100 spores/spot. Growth of the molds were assessed visually after storage for 36 days at 7° C.±1° C., 12° C.±1° C. or 22° C.±1° C.

Figure 12:
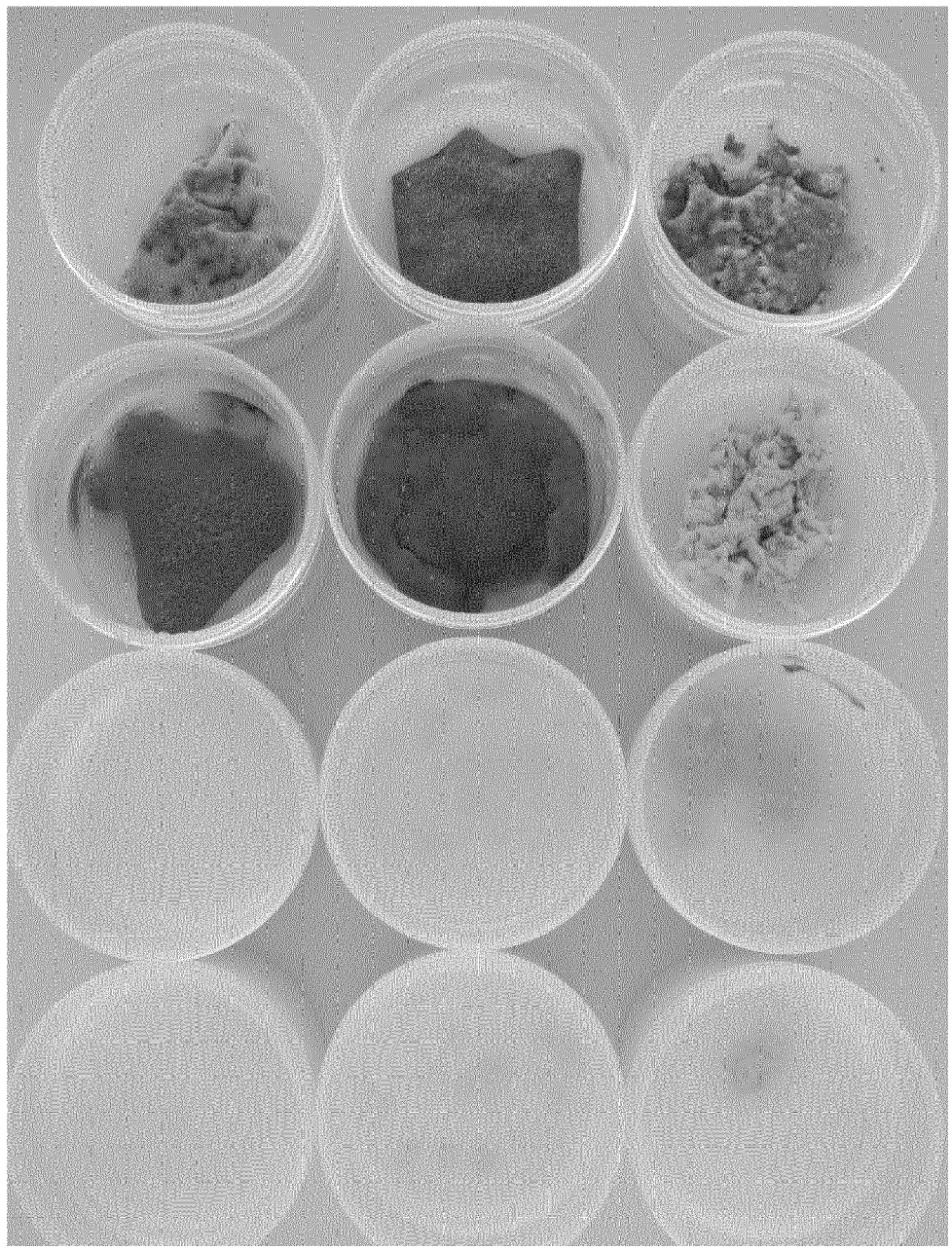
FIG. 12 shows growth of the mold *Penicillium crustosum* in yoghurt with 1.5% fat prepared from milk fermented with a starter culture alone (top row), with starter culture and HOLDBAC™ YM-B (second row), with starter culture and *Lactobacillus rhamnosus* CHCC5366 (third row) or with starter culture and a combination of *Lactobacillus rhamnosus* CHCC5366 and *Lactobacillus paracasei* CHCC14676 (bottom row). The target contaminant was added in the concentrations of 100 spores/cup and the yoghurts had been incubated at 7±1° C. (left column), 12±1° C. (centre column) or 22±1° C. (right column) for 36 days.

The result of the yoghurt test is presented in FIG. 12, showing that P. crustosum grows well on yoghurt made from milk fermented only with the starter culture YF-L901 or with the starter culture and the HOLDBAC™ YM-B culture at all storage temperatures. In contrast, when Lactobacillus rhamnosus CHCC5366 alone or in combination with Lactobacillus paracasei CHCC14676 was present during milk fermentation, growth of P. crustosum was completely prevented upon storage both at 7° C.±1° C. and 12° C.±1° C. for 36 days. Upon storage at 22° C.±1° C. growth of P. crustosum was strongly reduced in the presence of Lactobacillus rhamnosus CHCC5366 and even stronger in the presence of the combination of Lactobacillus rhamnosus CHCC5366 and Lactobacillus paracasei CHCC14676.

DEPOSITS AND EXPERT SOLUTION

The applicant requests that a sample of the deposited micro-organisms stated below may only be made available to an expert, until the date on which the patent is granted.

The Lactobacillus rhamnosus strain CHCC5366 was deposited 2009 Oct. 14 at German Collection of Microorganisms and Cell Cultures (Deutsche Sammlung von Mikroorganismen und Zellkulturen GmbH; DSMZ), Inhoffenstr. 7B, D-38124 Braunschweig and given the accession No.: DSM23035.

The Lactobacillus paracasei strain CHCC12777 was deposited 2011 Mar. 15 at German Collection of Microorganisms and Cell Cultures (Deutsche Sammlung von Mikroorganismen und Zellkulturen GmbH; DSMZ), Inhoffenstr. 7B, D-38124 Braunschweig and given the accession No.: DSM24651.

The Lactobacillus paracasei strain CHCC14676 was deposited 2012 Feb. 2 at German Collection of Microorganisms and Cell Cultures (Deutsche Sammlung von Mikroorganismen und Zellkulturen GmbH; DSMZ), Inhoffenstr. 7B, D-38124 Braunschweig and given the accession No.: DSM25612.

The deposit was made according to the Budapest treaty on the international recognition of the deposit of microorganisms for the purposes of patent procedure.

REFERENCES

EP0221499
EP0576780
EP1442113
U.S. Pat. No. 5,378,458
EP11161609.0
Kosikowski, F. V. and Mistry, V. V., "Cheese and Fermented Milk Foods", 1997, 3rd Ed. F. V. Kosikowski, L.L.C. Westport, Conn.

The invention claimed is:

1. An antifungal composition comprising at least one strain of *Lactobacillus rhamnosus* and at least one strain of *Lactobacillus paracasei*, wherein the composition comprises a *Lactobacillus rhamnosus* strain selected from the group consisting of *Lactobacillus rhamnosus* CHCC5366 with accession No. DSM23035 and mutant strains thereof, wherein the mutant strains have substantially the same or improved antifungal properties as compared to *Lactobacillus rhamnosus* CHCC5366, and wherein the composition comprises at least $5 \times 10^6$ cfu/g of the *Lactobacillus rhamnosus* CHCC5366 and at least $5 \times 10^6$ cfu/g of the *Lactobacillus paracasei*.

2. The antifungal composition according to claim 1, wherein the at least one strain of *Lactobacillus paracasei* is selected from the group consisting of *Lactobacillus paracasei* CHCC12777 with accession no. DSM24651 and *Lactobacillus paracasei* CHCC14676 with accession no. DSM25612 and mutant strains thereof, wherein the mutant strains have substantially the same or improved antifungal properties as compared to *Lactobacillus paracasei* CHCC12777 or *Lactobacillus paracasei* CHCC14676, respectively.

3. A method for preparing a food, feed or pharmaceutical product comprising adding the composition of claim 1 to the food, feed or pharmaceutical product during manufacture.

4. A method for inhibiting the growth of yeasts and molds in a food, feed, or pharmaceutical product comprising adding the composition of claim 1 to the food, feed, or pharmaceutical product.

5. A manufactured product comprising (a) a fruit, a fruit derived product, a vegetable, a vegetable derived product, a grain, a grain derived product, a dairy product, meat, poultry, seafood or mixtures thereof and (b) at least $1 \times 10^4$ cfu/g of at least one *Lactobacillus rhamnosus* strain selected from the group consisting of the *Lactobacillus rhamnosus* CHCC5366 with accession No. DSM23035 and mutant strains thereof, wherein the mutant strains have substantially the same or improved antifungal properties as compared to *Lactobacillus rhamnosus* CHCC5366.

6. The product according to claim 5 comprising an amount of the *Lactobacillus rhamnosus* strain effective for imparting antifungal properties to the product.

7. The product of claim 5, wherein the product is a food, feed or pharmaceutical product.

8. The food product according to claim 7, wherein the food product is a dairy product selected from the group consisting of mesophilic and thermophilic fermented milk products.

9. A method for manufacturing the product of claim 5, comprising adding the at least one *Lactobacillus rhamnosus* strain to the product during manufacture and controlling the manufacturing parameters during the manufacturing such that the concentration of the at least one *Lactobacillus rhamnosus* strain remains constant or is increased.

10. The method according to claim 9, wherein the concentration of the at least one *Lactobacillus rhamnosus* strain is at least $1 \times 10^6$ cfu/g or at least $1 \times 10^6$ cfu/ml of the product, or at least $1 \times 10^5$ cfu/cm$^2$ of the surface of the product.

11. The method according to claim 9, comprising
    (a) adding to the product, during the manufacture of the product, a composition comprising at least one strain of *Lactobacillus rhamnosus* and at least one strain of *Lactobacillus paracasei*, wherein the composition comprises a *Lactobacillus rhamnosus* strain selected from the group consisting of *Lactobacillus rhamnosus* CHCC5366 with accession No. DSM23035 and mutant strains thereof, wherein the mutant strains have substantially the same or improved antifungal properties as compared to *Lactobacillus rhamnosus* CHCC5366, and wherein the composition comprises at least $5 \times 10^6$ cfu/g of the *Lactobacillus rhamnosus* CHCC5366 and at least $5 \times 10^6$ cfu/g of the *Lactobacillus paracasei*, and
    (b) controlling the manufacturing parameters during the manufacturing such that the concentration of the at least one strain of *Lactobacillus rhamnosus* and/or the at least one strain of *Lactobacillus paracasei* increases or remains constant.

12. The method according to claim 9, wherein the method comprises one or more fermentation steps.

13. The method according to claim 12, wherein the method comprises fermenting a milk substrate with a starter culture comprising at least one strain of the genera selected from *Lactobacillus, Streptococcus, Lactococcus* and *Leuconostoc*.

14. A method of making the product of claim 5 comprising:
    adding the at least one *Lactobacillus rhamnosus* strain to a food product during manufacture, and
    controlling manufacturing parameters such that the concentration of the at least one *Lactobacillus rhamnosus* strain remains constant or is increased.

15. A method for preparing the product of claim 5 comprising adding the *Lactobacillus rhamnosus* strain to the product during manufacture.

16. A method for inhibiting the growth of yeasts and molds in the product of claim 5 comprising adding the *Lactobacillus rhamnosus* strain to the product during manufacture.

* * * * *